(12) United States Patent
Osswald et al.

(10) Patent No.: US 8,980,973 B2
(45) Date of Patent: Mar. 17, 2015

(54) SILOXANE COMPOUNDS CONTAINING COMPOSITION, METHOD OF PRODUCTION AND USE THEREOF

(75) Inventors: Peter Uwe Osswald, Tuerkheim (DE); Hyung-Min Shim, Gyeonggi-do (KR); Johann Fetz, Windach (DE); Joachim Wilhelm Zech, Kaufering (DE); Bernd Kuppermann, Herrsching (DE)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 14/124,456

(22) PCT Filed: Jun. 5, 2012

(86) PCT No.: PCT/US2012/040899
§ 371 (c)(1),
(2), (4) Date: Mar. 3, 2014

(87) PCT Pub. No.: WO2012/170413
PCT Pub. Date: Dec. 13, 2012

(65) Prior Publication Data
US 2014/0170599 A1 Jun. 19, 2014

(30) Foreign Application Priority Data

Jun. 8, 2011 (EP) .................................. 11169035

(51) Int. Cl.
| | | |
|---|---|---|
| *A61K 6/10* | (2006.01) | |
| *C08L 83/04* | (2006.01) | |
| *A61C 9/00* | (2006.01) | |
| *A61K 6/00* | (2006.01) | |
| *C08G 77/04* | (2006.01) | |
| *C08G 77/12* | (2006.01) | |
| *C08G 77/20* | (2006.01) | |

(52) U.S. Cl.
CPC ............. *A61C 9/0006* (2013.01); *A61K 6/10* (2013.01); *C08L 83/04* (2013.01); *A61K 6/005* (2013.01); *A61K 6/0058* (2013.01); *A61K 6/0088* (2013.01); *C08G 77/04* (2013.01); *C08G 77/12* (2013.01); *C08G 77/20* (2013.01)
USPC ........... 523/109; 524/261; 524/268; 524/588; 525/477; 525/478; 528/15; 528/31; 528/32

(58) Field of Classification Search
USPC ............. 523/109; 525/477, 478, 479; 528/15, 528/31, 32; 524/588
See application file for complete search history.

(56) References Cited

U.S. PATENT DOCUMENTS

| | | |
|---|---|---|
| 3,715,334 A | 2/1973 | Karstedt |
| 3,775,352 A | 11/1973 | Leonard |
| 3,814,730 A | 6/1974 | Karstedt |
| 3,933,880 A | 1/1976 | Bergstrom |
| 4,035,453 A | 7/1977 | Hittmair |
| 4,273,902 A | 6/1981 | Tomioka |
| 4,609,687 A | 9/1986 | Schwabe |
| 4,657,959 A | 4/1987 | Bryan |
| 4,879,339 A | 11/1989 | Yoshino |
| 4,891,400 A | 1/1990 | Schwabe |
| 5,064,891 A | 11/1991 | Fujiki |
| 5,066,714 A | 11/1991 | Inoue |
| 5,249,862 A | 10/1993 | Herold |
| 5,286,105 A | 2/1994 | Herold |
| 5,332,122 A | 7/1994 | Herold |
| 5,464,131 A | 11/1995 | Keller |
| 5,684,060 A | 11/1997 | Konings |
| 5,750,589 A | 5/1998 | Zech |
| 5,849,812 A | 12/1998 | Zech |
| 5,924,600 A | 7/1999 | Keller |
| 6,135,631 A | 10/2000 | Keller |
| 6,244,740 B1 | 6/2001 | Wagner |
| 6,569,914 B2 * | 5/2003 | Zoellner et al. .................. 522/99 |
| 6,677,393 B1 | 1/2004 | Zech |
| 6,838,499 B2 | 1/2005 | Kimura |
| 6,894,144 B1 | 5/2005 | Zech |
| 7,186,758 B2 | 3/2007 | Zech |
| 8,466,210 B2 * | 6/2013 | Zech et al. .................... 523/109 |
| 2004/0085854 A1 | 5/2004 | Pauser |

FOREIGN PATENT DOCUMENTS

| | | |
|---|---|---|
| DE | 19719438 | 11/1997 |
| EP | 0232733 | 10/1989 |
| EP | 0398745 | 9/1996 |
| EP | 1165016 | 1/2001 |
| EP | 0730913 | 10/2001 |
| EP | 0863088 | 5/2004 |
| EP | 1083860 | 10/2004 |
| EP | 1290998 | 3/2005 |
| EP | 1353625 | 3/2009 |
| WO | WO 2007-001896 | 1/2007 |

OTHER PUBLICATIONS

3M ESPE, "Pentamix™ 2 Automatic Mixing Unit", 2010, 6 pages.
Schott, "Hydrophile-Lipophile Balance and Cloud Points of Nonionic Surfactants", Journal of Pharmaceutical Science, Dec. 1969, vol. 58, No. 12, pp. 1443-1449.
International Search Report for PCT International Application No. PCT/US2012/040899 Mailed on Jul. 23, 2012, 3 pages.

* cited by examiner

Primary Examiner — Marc Zimmer

(57) ABSTRACT

The invention relates to a composition for taking dental impressions, the composition comprising a siloxane component (A) comprising terminal vinyl groups, a siloxane component (B) comprising Si—H groups, a catalyst (C) being able to catalyze a curing reaction between components (A) and (B) and a silicone oil (D), wherein the silicone oil has a viscosity at 23 DEG C of at least about 600,000 mPa*s and is present in an amount from about 1 to about 20 wt.% with respect to the weight of the whole composition. The invention also relates to a method of producing such a composition and a method for adjusting the Shore hardness A of a composition.

42 Claims, No Drawings

US 8,980,973 B2

SILOXANE COMPOUNDS CONTAINING COMPOSITION, METHOD OF PRODUCTION AND USE THEREOF

FIELD OF THE INVENTION

The invention relates to hardenable siloxane compounds containing compositions which comprise a high viscous silicone oil. This composition can in particular be used in the dental field, e.g. for taking dental impressions.

BACKGROUND ART

Materials applicable for dental impression are well known in the art.

Commonly used classes of impression materials are based on addition- or condensation crosslinking-reactions of polyorganosiloxane containing components as described e.g. in U.S. Pat. No. 5,064,891, EP 0 729 341 A1 or U.S. Pat. No. 4,657,959 or on crosslinkable polyethers, e.g. so-called azridino-polyethers as described e.g. in EP 1 210 055 B1.

Recently, hybride materials of polyorganosiloxanes and polyether as described e.g. in EP 1 290 998 A1 and DE 19719438 B4, are available.

The mentioned materials typically possess a variety of properties including a quick setting behaviour and a good dimensional stability. Generally, the materials are provided in two components to be mixed prior to use.

Besides the curing mechanism, impression materials can be classified according to their consistencies (ISO 4823) as putty materials (type 0, consistency ≤35 mm), heavy-bodied materials (type 1, consistency ≤35 mm), medium-bodied (type 2, consistency=31-41 mm) and light-bodied (type 3, consistency ≥36 mm). Among those, putty type impression materials are widely used as tray materials.

Addition or condensation cured silicone impression materials which contain C8-C24 Isoparafin are described in EP 0219660 A2.

U.S. Pat. No. 4,879,339 describes an addition cured silicone composition with putty consistency comprising apart from vinyl-functionalized organopolysiloxanes, a crosslinker, Pt-catalyst and filler, a paraffin oil and an antioxidant. Herein the paraffin oil is used to adjust the handling properties of the putty, whereas the antioxidant ensures the stability of the aliphatic component.

The use of paraffin-loaded fillers in dental silicone-based impression materials is described in DE 3406233A 1. The preloading of the filler prevents sweating of paraffin oil from the pastes and the cured product.

EP 1 083 860 B1 describes very high viscous impression materials containing a QM resin and a vinyl-terminated polydimethylsiloxane with a molecular weight of 400000 to 500000 g/mol which makes the material non-sweating.

U.S. Pat. No. 6,838,499 B2 describes a curable composition which includes elastomer powder and is tack-free and easy to work. According to the description it can comprise a dihydroxy-functionalized silicone oil with a viscosity of up to 1,000,000 mPa*s for condensation curable putty formulations or a divinylterminated silicone oil with a viscosity of up to 10,000,000 mPa*s for addition cured silicone compositions although no examples are given.

U.S. Pat. No. 5,066,714 describes a curable organopolysiloxane putty-like composition which comprises apart from divinylpolysiloxanes, crosslinker, catalyst and filler an organopolysiloxane with at least to different alkyl substituents as release agent.

EP 0 398 745 B1 describes a curable silicone composition a hydrophlized addition-cured silicone impression material which might contain a vinyl-terminated organopolysiloxane with a viscosity of up to 5,000,000 mPa*s.

Recently, also automix putty materials have been made available as e.g. described in EP 1 372 575 B1 or EP 1 353 625 B1.

DESCRIPTION OF THE INVENTION

However, there is still a need for improved products.

E.g. there is a need for a dental impression material or a material for use in a dental impression making process, which allows the adjustment of the Shore hardness without changing the consistency.

If possible, the material should also be essentially tack-free.

Moreover, if possible, the material should be sufficient storage stable.

It was found that one or more of these objects can be solved with a composition for taking dental impressions, the composition comprising a) a siloxane component (A) comprising terminal vinyl groups b) a siloxane component (B) comprising Si—H groups c) a catalyst (C) being able to catalyze or initiate a curing reaction between components (A) and (B), d) a silicone oil (D), e) optionally a filler (E), f) optionally a surfactant (F), g) optionally adjuvants (G), wherein the silicone oil has a viscosity of at least about 600,000 mPa<*>s or of at least about 800,000 or at least about 1,000,000 mPa<*>s (equal to cSt) and is present in an amount from about 1 to about 20 wt.-% with respect to the weight of the whole composition.

The invention also relates to a kit of parts to be used for taking dental impressions, the kit comprising a base part and a catalyst part, the base part comprising at least component (B), the catalyst part comprising at least catalyst (C) and component (A), wherein components (A), (B), (C), (D), (E), (F) and (G) are as described in the present text.

The invention also features a method of producing a composition having a consistency of ≤41 mm or ≤35 mm according to ISO 4823, the method comprising the step of mixing a siloxane component (A) comprising terminal vinyl groups, a siloxane component (B) comprising Si—H groups, a catalyst (C) being able to initiate the hardening reaction between components (A) and (B) with a silicone oil (D), wherein silicone oil is present in an amount from about 1 to about 20 wt.% with respect to the weight of the whole composition, the silicone oil having a viscosity of at least about 600,000 mPa<*>s or at least about 800,000 or at least about 1,000,000 mPa<*>s, A further aspect of the invention is directed to the use of a silicone oil for adjusting the Shore hardness of a composition having a consistency of ≤41 mm or ≤35 mm according to ISO 4823, the composition comprising a siloxane component (A) comprising terminal vinyl groups, a siloxane component (B) comprising Si—H groups, a catalyst (C) being able to initiate the hardening reaction between components (A) and (B), wherein the silicone oil has a viscosity of at least about 600,000 mPa*s and is used in an amount from about 1 to about 20 wt. % with respect to the weight of the whole composition as described in the present text.

According to a further aspect, the invention is directed to a process of adjusting the Shore hardness of a composition comprising a base formulation (I) and a catalyst formulation (II) by varying the volume ratio of base formulation (I) and catalyst formulation (II) within a range from about 1:1 to about 30:1 as described in the present text.

DETAILED DESCRIPTION

Within the description of the invention, the following terms are defined as follows:

The term "compound or component" is a chemical substance which has a particular molecular identity or is made of a mixture of such substances, e.g., polymeric substances.

The term "hydrosilation" means the addition of an organosilicone hydride compound to a compound containing an aliphatic multiple bond (e.g., an olefinic or acetylenic unsaturation), preferably a vinyl group, $-CH=CH_2$.

By "paste" is meant a soft, viscous mass of solids dispersed in a liquid.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

A "hardenable matrix" may be described as the components of a composition contributing to the formation of a network due to chemical interaction (e.g. formation of chemical bondings) between the components thereby leading to a significant change in rheological properties like viscosity.

The terms "vulcanizing, hardening, crosslinking, setting," are used interchangeable and refer to silicones that have as a common attribute the development of a crosslinked elastomer from relatively low molecular weight linear or branched polymers by means of a chemical reaction that simultaneously forms these crosslinks and effectively extends chain length at room temperature. "Room temperature vulcanizing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods.

The term "crosslinked polymer," as used herein, refers to polymers that react with the functional group or groups of the polymer chains to lengthen them and connect them, e.g., to form a crosslinked network characteristic of a silicone elastomer. In contrast to a thermoplastic polymer (i.e., a polymer that softens and flows upon heating) a crosslinked polymer, after crosslinking, is characteristically incapable of further flow.

A "dental compositions and dental articles" within the meaning of the present invention is a composition which is to be used in the dental field (including restorative and prosthodontic work) including the orthodontic area. In this respect, a dental composition typically does not contain hazardous substances. Commercially available products have to fulfill certain requirements such as those given in ISO 4823. Typically, those compositions cure or set at ambient conditions.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are sodium alginate, agar, polyethers including aziridino substituted polyether materials and silicones, both condensation-cured silicones and addition-cured silicones including polyvinyl siloxanes.

The term "automixer-suitable impression material" relates to a multi-component impression material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™" and "Pentamix™ 2" devices of 3M ESPE Company (cf. U.S. Pat. No. 5,286,105 and 5,249,862).

The term "dental tissue" includes the hard tooth substance (enamel and dentin), the gingival region (soft dental tissue) surrounding the hard tooth substance and hard tooth substance bearing orthodontic appliances.

Surfactants, also sometimes referred to as tensides, are wetting agents that are able to lower the surface tension of a liquid, allowing easier spreading, and lower the interfacial tension between two liquids.

Surfactants are usually organic compounds that are amphiphilic, meaning they contain both hydrophobic groups ("tails") and hydrophilic groups ("heads"). Typical examples include polyethyleneglycol-substituted fatty acids.

Usually, a surfactant can be classified by the presence of formally charged groups in its head. A nonionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Surfactants typically reduce the surface tension of water by adsorbing at the liquid-gas interface. They also may reduce the interfacial tension between oil and water by adsorbing at the liquid-liquid interface. Many surfactants can also assemble in the bulk solution into aggregates. Some of these aggregates are known as micelles. The concentration at which surfactants begin to form micelles is known as the critical micelle concentration (CMC).

Surfactants can also be characterized by a "Hydrophobic Lipophilic Balance" value (HLB-value). Generally, with an increasing HLB-value a substance becomes more hydrophobic and in reverse more lipophilic. The measurement of the HLB-value of a certain substance can be accomplished by determining its aqueous solubility and cloud point, using e.g. the method described by H. Schott, J. Pharm. Science, 58, 1442, (1969). E.g. according to the product description, Silwett L-77 (a Si-containing surfactant) is said to have an estimated HLB value in the range of 5 to 8.

The term "working time" as used herein, refers to the time between the initiation of the setting reaction (e.g., when the vinyl-containing organopolysiloxane, the organohydropolysiloxane, and the platinum catalyst are mixed) and the time the setting reaction has proceeded to the point at which it is no longer practical to perform further physical work upon the system, e.g., reform it, for its intended purpose. When the reaction has proceeded to this later point the material is said to have reached its "gel point." The working time preferably provides enough time to mix and place the composition into its desired form. For many dental impression compositions and applications the working time under conditions of use can be greater than about 30 s (seconds), or greater than about 1 min (minute), or greater than about 2 min. Thus, the working time is typically within a range of about 30 s to about 3 min or about 1 min to about 2 min. So-called "fast-setting" compositions typically have a shorter working time, e.g. less than about 2 min or less than about 1.5 min.

The terms "set time" or "setting time" as used herein, refer to the time at which sufficient curing has occurred so that essentially the material's final cured-state properties are obtained. For a silicone impression material the set time is that time at which one may remove the material from the surface being replicated without causing permanent deformation of the silicone material. The setting time may be approximated, for example, by measuring the torque of the reacting composition on an oscillatory rheometer. When the torque value reaches a maximum value the material is said to be fully set. An arbitrary torque value which is less than the typical maximum value (e.g. 90% of the maximum value) may alternatively be used as a practical approximation of the set time. In general, shorter setting times are preferred over longer setting times. For dental impression compositions the setting time occurs at a time preferably less than about 10 minutes after initiation of the reaction. More preferably the setting time is less than the sum of about 5 minutes plus the working time. Most preferably the setting time is just longer than the desired working time.

More specifically, the setting time is the time between positioning of the spoon with the dental material in the mouth of the patient and removal of the cured material, and can also be called the mouth residence time or period. Setting times of < about 3 min mouth residence time, preferably < about 2.5 min, and particularly preferably < about 2 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

If desired, the setting time of the compositions can be determined by measuring the viscosity in dependence on the time at 33° C. by using a MDR 2000 rheometer from Alpha instruments under aerobic conditions at 50% humidity. The setting time can be determined as the $t_{90}$ value, at which 90% of the final viscosity was achieved. Another characteristic size is the $t_5$ value, at which 5% of the final viscosity was present. Until this time the composition can be assumed to be almost free of network formation (curing).

By a (temporary or long term) crown and bridge material is meant a material, which is used for the preparation of dental crowns and bridges containing hardenable monomers, including (meth)acrylates. These materials are typically used during the time period needed for making a permanent restoration. A typical time period ranges from a few days (e.g. 3 to 5) over weeks (1 to 3) to a few months (1 to 6). A long term crown and bridge material is typically used over a time period of about 6 to about 24 month.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and about 1013 mbar. Ambient conditions in the oral cavity of a patient typically include a temperature of about 36° C.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." The numerical values set forth in the specific examples are reported as precisely as possible. Any numerical value, however, inherently contains certain errors necessarily resulting from the standard deviations found in their respective testing measurements.

It was found that the addition or use of a silicone oil with a molecular weight of at least about 600,000 mPa*s in an amount varying from about 1 to about 20 wt.-% with respect to the weight of the whole composition facilitates adjusting the Shore hardness of a curable composition, however, without essentially affecting the consistency, which is typically measured according to ISO 4823.

Contrary to the expectation that the addition of a silicone oil will also influence the consistency of the composition (e.g. from a highly viscous stage to a more moderate viscosity), it was surprisingly found that this is not the case, if certain conditions are met, like molecular weight and amount of the silicone oil used.

This can especially be beneficial from a production standpoint of view. A variety of hardenable compositions having different Shore hardnesses after hardening can easily be provided simply by adding a certain amount of a silicone oil with a certain molecular weight to a hardenable (master) batch composition.

Certain embodiments of the curable composition before hardening can be characterized by at least one of the following features before hardening:
  Consistency (according to ISO 4823): 0,
  Setting time: within about 15 min after mixing at a temperature in the oral environment (about 36° C.).

That is, the curable dental composition shows a putty-like behaviour (consistency 0).

Certain embodiments of the curable composition before hardening can be characterized by at least one of the following features:
  Consistency (according to ISO 4823): 2,
  Setting time: within about 15 min after mixing at a temperature in the oral environment (about 36° C.).

That is, the curable dental composition may also show a monophase-like behaviour (consistency 2).

Certain embodiments of the cured composition (that is, after hardening) can be characterized by at least one of the following features:
  Tensile strength (according to DIN 53504): at least about 0.2 MPa, or at least about 1.0 or at least about 2.0,
  Elongation at break (according to DIN 53504): at least about 30%, or at least about 60%, or at least about 100%,
  Recovery from deformation (according to ISO 4823): at least about 90%, or at least about 95%, or at least about 98%,
  Shore A hardness (according to ISO 4823; 24h): at least about 20 or at least about 40.

In particular, if desired, the tensile strength and elongation of the compositions can be determined according to DIN 53504. The tensile strength is typically given in MPa and the elongation in % of the original length. Tensile strength and elongation data can be evaluated by tearing six I-shaped specimens with a central unit of 20 mm×4 mm×2 mm in a Zwick Z020 Universal testing machine. Base and catalyst pastes are typically mixed through a static mixer (SulzerMixpac Comp.) and filled into a brass mould. After 3 h at 23° C.

the specimen are removed, six measurements are made and the mean value determined (speed 200 mm/min).

The composition contains as component (A) a curable silicone polymer containing at least two functional groups capable of reacting with a SiH group in the presence of a hydrosilation catalyst.

Typically, the curable silicone polymer is an organopolysiloxane with at least two pendant or terminal triorganosiloxy groups in which at least one of the three organic groups is a group with an ethylenically unsaturated double bond.

Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula (I)

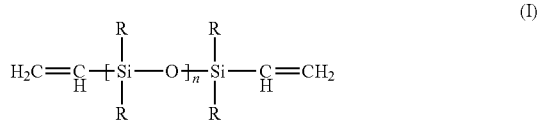

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the organopolysiloxanes lies between about 20 and about 500,000 mPas or between about 30 and about 300,000 or between about 50 and about 100,000 mPas. The parameter n can, e.g., be in the range of about 3 to about 4,000; "n" is typically within a range of about 10 to about 4000 or from about 20 to about 3500.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment of the invention, at least about 50% of the radicals R are methyl groups. Examples of other radicals R that can be present in the organopolysiloxanes according to the above formula are ethyl, propyl, iso-propyl, n-butyl, iso-butyl, tert-butyl, the pentyl isomers, the hexyl isomers, vinyl, propenyl, iso-propenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is regarded as being part of the disclosure of the present document and is included herein by reference.

The preparation of molecules according to the above-mentioned formula would generally be understood by the skilled person based upon the teachings of the prior art regarding similar molecules.

Particularly preferred are linear polydimethylsiloxanes according to the above formula having viscosities within the specified viscosity ranges and end groups comprising dimethylvinylsiloxy units and methyl groups as the radicals R.

A component (A) which can be employed can consist of one type (A1) of organopolysiloxane. The organopolysiloxane can have a viscosity starting in the range of about 20 to about 500,000 mPas, or about 30 to about 300,000 mPas or about 50 to about 100,000 mPas.

It is, however, also possible that component (A) comprises two or more constituents, (A1), (A2) and so on, which can differ, e.g., in the chemical composition of their backbone, or their molecular weight, or their substituents or their viscosity, or any other differentiating feature or two or more of the above mentioned features.

In one embodiment of the invention the difference in viscosities of different constituents of component (A) can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselves.

In some embodiments it can be beneficial if a high viscous unsaturated organopolysiloxane is used as component (A) or as part of component (A), e.g. in a range of about 500,000 mPas to about 10,000,000 mPas. This may facilitate the handling properties especially of a hand-mix putty composition.

If desired, the viscosity can be measured using a Haake Rotovisco RV20 device (spindle MV, measuring cup NV). The viscosity is typically measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

If component (A) contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from about 1:20 to about 20:1, especially about 1:10 to about 10:1 or about 1:6 to about 6:1. It can furthermore be adequate in some cases, when the amount of constituent with the highest viscosity is about equal to or higher than the amount of constituent with the lowest viscosity, resulting in a value of from about 0.9:1 to about 10:1 for the ratio of the amount of constituent with the highest viscosity to the amount of constituent with the lowest viscosity. All of the ratios are based on the weight of the constituents.

Compound (A) is typically present in an amount of at least about 8 or at least about 10 wt.-% with respect to the amount of the whole composition.

Compound (A) is typically present in an amount below about 60 or below about 55 wt.-% with respect to the amount of the whole composition.

Typical ranges for compound (A) include from about 8 wt.-% to about 60 wt.-% or from about 10 wt.-% to about 55 wt.-%.

The composition further comprises as component (B) or part of component (B) a crosslinker compound containing at least two or three SiH groups.

By definition, an organohydrogenpolysiloxane according to the present text does not belong to the group of organopolysiloxanes used as component (A) or part of component (A) as described in the context of the invention.

An organohydrogenpolysiloxane typically contains from about 0.01 to about 1.7 wt.-% silicon-bonded hydrogen or from about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component (B) include those having a viscosity of about 10 to about 1,000 mPas or from about 15 to about 550 mPas or from about 20 to about 250 mPas.

Compound (B) is typically present in an amount of at least about 0.1 or at least about 1 wt.-% with respect to the amount of the whole composition.

Compound (B) is typically present in an amount below about 20 or below about 18 wt.-% with respect to the amount of the whole composition.

Typical ranges for compound (B) include from about 0.1 to about 20 or from about 1 to about 18 wt.-% with respect to the amount of the whole composition.

The composition also contains a catalyst as component (C) or as a part of component (C) capable of catalyzing a hydrosilation reaction.

This catalyst is typically a platinum catalyst or a platinum containing catalyst, including a platinum complex which can be prepared from hexachloroplatinum acid by reduction with tetramethyldivinyldisiloxane. Such compounds are known to the skilled person. Any other compounds which catalyze or accelerate addition cross-linking of silanes with ethylenically unsaturated double bonds are also suitable. Platinum-siloxane complexes as described, e.g. in U.S. Pat. Nos. 3,715,334; 3,775,352 and 3,814,730 are suitable. The disclosure of these patents with regard to platinum complexes and their preparation is explicitly mentioned and expressly regarded as part of the disclosure of the present text.

The catalyst can typically be used in an amount of about 0.00005 to about 0.05 wt.-%, particularly about 0.0002 to about 0.04 wt. %, each calculated as elemental platinum and related to the overall weight of the composition.

Components (A), (B) and (C) belong to the the hardenable matrix of the composition.

The inventive composition comprises a silicone oil as component (D). The silicone oil can be characterized by at least one of the following features:
  Molecular weight (Mw): of at least 250.000 g/mol or of at least 300.000 g/mol;
  Viscosity: of at least about 600.000 mPa*s or of at least about 800.000 or at least about 1.000.000 mPa*s (at about 23° C.);
  End-capped with moieties selected from saturated groups including trimethylsiloxy-groups.

According to one embodiment, the silicone oil can be characterized by the following formula:

(I)

with n of at least about 3500 or at least about 4000 R1 being independently selected from C1-C6 alkyl or C6-C9 aryl.

If the molecular weight of the silicone oil is below about 260.000 g/mol, the desired effect of being able to influence the Shore hardness while essentially maintaining the consistency will be difficult to obtain.

Particular examples of silicone oils which can be used, include polydimethylsiloxanes with a viscosity of about 1,000,000 mPas or about 2,000,000 mPas obtainable e.g. from Momentive or Wacker company.

The silicone oil (D) is typically present in an amount of at least about 1 wt.-% with respect to the amount of the whole composition.

The silicone oil (D) is typically present in an amount below about 20 or below about 15 wt.-% or below about 10 wt.-% with respect to the amount of the whole composition.

Typical ranges for the silicone oil (D) include from about 1 to about 20, or from about 1 to about 15 wt.-% or about 1 to about 10 wt.-% with respect to the amount of the whole composition.

If the silicone oil is present in the composition in a higher or lower amount, the desired result of essentially maintaining the consistency while influencing the Shore hardness may be difficult to obtain.

In particular, if the silicone oil is used in an amount above about 20 wt.-%, the silicone oil may dilute the reactive components to an extent that the setting reaction can be adversely affected or the surface may start to get sticky.

On the other hand, if the silicone oil is used in an amount below about 1 wt.-%, it tends to become difficult to influence the Shore hardness.

The composition may also contain a filler or a mixture of fillers, e.g. as component (E) or as a part of component (E), even if the presence of a filler is not mandatory. The nature of the filler is not particularly limited.

Typically filler can be used in an amount of from of at least about 5 wt.-% or at least about 20 or at least about 35 wt.-% with respect to the whole composition.

There is no particular upper limit, however, typically the amount of filler, if present at all, is used in an amount of at most about 85 wt.-% or at most about 80 wt.-% with respect to the whole composition.

Thus, typical ranges for the filler as component (E) include from about 5 to about 85 or from about 20 to about 80 wt.% with respect to the whole composition.

A wide variety of inorganic, hydrophilic or hydrophobic fillers may be employed such as silicas, aluminas, magnesias, titanias, inorganic salts, metallic oxides and glasses. It has been found to be possible to employ mixtures of silicon dioxides, including those derived from crystalline silicon dioxide, such as pulverized quartz (4-6 μm); amorphous silicon dioxides, such as a diatomaceous earth (4-7 μm); and silanated fumed silica, such as Cab-o-Sil TS-530 (160-240 m$^2$/g), manufactured by Cabot Corporation.

The sizes and surface areas of the foregoing materials can be adjusted to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes. Such fillers can be present in amounts of from about 20 to about 85% by weight, especially about 25 to about 80 wt.-% of the material.

Among the fillers which can be used are fillers such as quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder.

Suitable fillers are also pyrogenic or precipitated silicic acid and silica aluminium mixed oxides. Those filler are commercially available from companies like Wacker or Degussa under the trade names Aerosil™, HDK-H.

The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 μm.

A combination of reinforcing and non-reinforcing fillers can be preferred. In this respect, the quantity of reinforcing fillers can range from about 0 to about 10 wt.-%, in particular from about 1 to about 7 wt.-% with respect to the whole composition.

Typical reinforcing fillers include fumed silica, carbon black and the like. They also can be surface treated and can improve mechanical properties like tensile strength or tear strength, of the cured silicone composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Preferred non-reinforcing fillers are quartzes, cristobalites and sodium aluminium silicates which can be surface-treated. The surface treatment can generally be carried out with the same methods as described in the case of the strengthening fillers.

Typical non-reinforcing fillers are quartz, precipitated silicas, diatomaceous earth, aluminas, magnesias, titanium dioxide, zirconium silicate, metallic oxides, and the like. These fillers can be surface treated, e.g. silanated, or non surface treated. Typical particle sizes are about 2 to about 10 μm.

The dental composition may also comprise a surfactant. Suitable surfactants include those which can be characterized by formula (II)

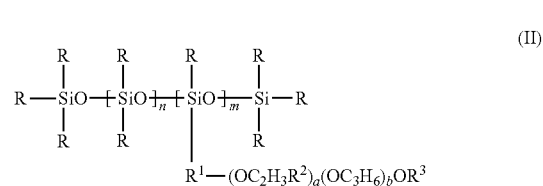

where each R is independently a monovalent hydrocarbyl radical with 1 to 22 C-atoms, R$^1$ is a divalent hydrocarbylene radical 1 to 26 C-atoms, each R$^2$ is independently hydrogen or a lower hydroxyalkyl radical, R$^3$ is hydrogen or a monovalent hydrocarbyl radical with 1 to 22 C-atoms, n and b are independently greater than or equal to 0, and m and a are independently greater than or equal to 1.

Other surfactants which can be used include those which can be represented by the following formula (III)

with Q being R$_3$—Si— or R$_3$—Si—(R'—SiR$_2$)$_a$—R'—SiR"$_2$, where each R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms; R' is a C$_1$-C$_{14}$ alkylene group; R" is R in the case of a≠0 or is R or R$_3$SiR' in the case of a=0, and a=0 to 2; P stands for a C$_2$-C$_{18}$ alkylene group, or A-R''', where A represents a C$_2$-C$_{18}$ alkylene group and R''' a functional group from the following list: —NHC(O)—, —NHC(O)—(CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH(OH)CH$_2$OC(O)(CH$_2$)$_v$C(O)— with v=1 to about 12; T is H or stands for a C1 to C4 alkyl radical or a C1 to C4 acyll radical; x stands for a number from 1 to about 200 and n stands for an average number from 1 to about 6.

If desired, also mixtures of different surfactants can be used.

Surfactants can be present in the inventive composition in an amount of more than about 0.01 wt.-%, with respect to the weight of the whole composition. If present, it can be preferred if the amount of component (F) is in a range of from about 0.1 to about 15 wt. % or from about 0.5 to about 8 wt.-% or from about 1 to about 5 wt.-% with respect to the weight of the whole composition.

According to a further embodiment, the inventive composition can also contain other additives or adjuvants e.g. as component (G) or part of component (G).

Those additives include retarders to modify the working and setting time (e.g. 3-methyl-I-butyne-3-ol or 1,1,3,3-tetramethyl-1,3-divinyl siloxane (VMO)), rheology modifiers (e.g. synthetic or natural waxes or polyethylene/propylene diacetats as described in EP 1 165 016 A1; corresponding to U.S. Pat. No. 6,677,393), pigments, dyes, plastizers (including paraffin oil or mineral oil), odorous substances, flavourings, stabilizers (including diphosphite(s) as described e.g. in WO 2007/001896 A2) alone or in admixture.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the invention. Examples of such inhibitors include acetylenic unsaturated alcohols such as 3-methyl-I-butyne-3-ol, 1-ethynylcyclohexane-I-ol, 3,5-dimethyl-I-hexyne-3-ol and 3-methyl-I-pentyne-3-ol. Examples of inhibitors based an vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups.

The composition may also contain a component useful for diminishing the presence or degree of hydrogen outgassing (sometimes also referred to as hydrogen scavenger) which may be typically generated as a result of the vinyl polymerization. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m$^2$/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal as described e.g. in U.S. Pat. No. 4,273,902 or Pd compounds as disclosed in to U.S. Pat. No. 5,684,060 can be employed.

The additive(s) can be present in an amount in the range of about 0.01 to about 90% by weight, or in the range of about 0.1 to about 40% by weight with respect to the cured composition.

Besides or alternatively to the surfactant(s) mentioned above, the composition may also comprise an F-containing component (H), wherein the F-containing compound is characterized by formula (IV)

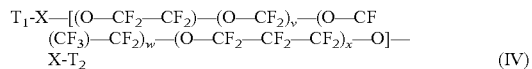
$$T_1-X-[(O-CF_2-CF_2)_u-(O-CF_2)_v-(O-CF(CF_3)-CF_2)_w-(O-CF_2-CF_2-CF_2)_x-O]-X-T_2 \quad (IV)$$

with u=0 to 8, v=0 to 8, w=0 to 8 and x=0 to 8 and u+v+w+x≥1, wherein $T_1$ and $T_2$ can be equal or different and are independently selected from —COOR, —CH$_2$OH, —CF$_2$OR, —CHFOH, —CHFOR, —CH$_2$OR or —F with R being a linear or branched alkyl rest (C1 to C9), aryl rest (C1 to C9) or alkylaryl rest (C1 to C9), and wherein X is selected from —(CF$_2$)$_{1-6}$—, —CF(CF$_3$)— and —CHF—CF$_2$—.

Useful F-containing compound also include those being characterized by formula (V)

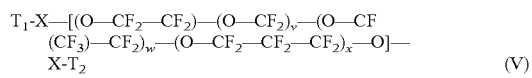
$$T_1-X-[(O-CF_2-CF_2)_u-(O-CF_2)_v-(O-CF(CF_3)-CF_2)_w-(O-CF_2-CF_2-CF_2)_x-O]-X-T_2 \quad (V)$$

with u=0 to 8, v=0 to 8, w=0 to 8 and x=0 to 8 and u+v+w+x≥1, wherein $T_1$ and $T_2$ can be equal or different and are independently selected from —COOR, —CH$_2$OH, —CF$_2$OR, —CHFOH, —CHFOR, —CH$_2$OR or —F with R being a linear or branched alkyl rest (C1 to C9), aryl rest (C1 to C9) or alkylaryl rest (C1 to C9), and wherein X is selected from —(CF$_2$)$_{1-6}$—, —CF(CF$_3$)— and —CHF—CF$_2$—.

If present, the F-containing component can be present in an amount below about 5 or below about 4 wt.-% with respect to the amount of the whole composition.

Typical ranges for the F-containing component include from about 0 to about 5, or from about 0.1 to about 4 wt.-% with respect to the amount of the whole composition.

It can be preferred if the F-containing component (H) is present together with a surfactant as described above. The presence of both components might lead to an improved wettability of the composition.

According to one embodiment of the invention, the composition can comprise the individual components in the following amounts:

Component (A): from about 10 wt.-% to about 60 wt.-% or from about 12 wt.-% to about 55 wt.-% with respect to the whole composition.

Component (B): from about 0.1 wt.-% to about 20 wt.-% or from about 1 wt.-% to about 18 wt.-% with respect to the whole composition.

Component (C): from about 0.001 wt.-% to about 0.1 wt.-% or from about 0.002 wt.-% to about 0.02 wt.-% or from about 0.005 wt.-% to about 0.01 wt.-% with respect to the whole composition.

Component (D): from about 1 wt.-% to about 20 wt.-% or from about 1 wt.-% to about 15 wt.-% with respect to the whole composition.

Component (E): from about 5 wt.-% to about 85 wt.-% or from about 20 wt.-% to about 80 wt.-% with respect to the whole composition.

Component (F): from about 0 wt.-% to about 15 wt.-% or from about 0 wt.-% to about 8 wt.-% or from about 0 wt.-% to about 5 wt.-% with respect to the whole composition.

Component (G): from about 0.01 wt.-% to about 90 wt.-% or from about 0.1 wt.-% to about 40 wt with respect to the whole composition.

Component (H): from about 0 wt.-% to about 5 wt.-% or from about 0.1 wt.-% to about 4 wt.-% with respect to the whole composition.

The composition is typically provided as a multi component material which comprises at least a curable base paste and a catalyst paste. The catalyst paste comprises a catalyst for curing at least part of the material of the base paste.

Accordingly, the components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base paste and a catalyst pate separated from each other before use, wherein the base paste comprises components (A) and (B), and the catalyst paste comprises component (C) or (C) and (A), and wherein components (D), (E), (F) and (G) if present are either present in the base paste or the catalyst paste or present in the base paste and the catalyst paste.

The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

The invention also relates to a method of producing a curable composition comprising the step of combining the silicone oil compound as described in the present text with a composition comprising components (A), (B), (C), wherein components (A), (B) and (C) are as described in the present text.

Thus, according to a further embodiment the invention is also directed to a method of producing the composition and/or adjusting the Shore hardness of a composition having a consistency of <41 mm or <35 mm according to ISO 4823, the method comprising the steps of providing a formulation comprising
a siloxane component (A) comprising terminal vinyl groups,
a siloxane component (B) comprising Si—H groups,
adding to the formulation a silicone oil (D), in an amount from about 1 to about 20 wt.-% with respect to the weight of the whole composition, the silicone oil (D) having a viscosity of at least about 600,000 mPa<*>s, thus obtaining a base paste,
mixing the base paste with a catalyst paste comprising
a siloxane component (A) comprising terminal vinyl groups and
a catalyst (C) being able to catalyze a curing reaction between components (A) and (B), wherein the siloxane component (A) of the base paste and the siloxane component (A) of the catalyst paste can be same or different and wherein either the base paste or the catalyst paste or both, the base paste and the catalyst paste can further comprise filler (E), surfactant (F), and adjuvants (G), wherein components (A), (B), (C), (D), (E), (F) and (G) are as described in the present text.

It was found that the Shore hardness can be adjusted by varying the amounts of silicone oil used without influencing the consistency of the (mixed) composition by more than about 50% or by more than 45% or by more than 40%.

This finding facilitates the production of a variety of compositions having a different Shore hardness after hardening, especially a different Shore A hardness.

A typical process of production can be described as follows:

A (master) batch is provided comprising siloxane component (A), siloxane component (B), optionally surfactant(s), filler(s), plastiziser(s) and other adjuvants like those described above.

To this (master) batch silicone oil (D) is added in the desired amount. By doing this, different base paste formulations are obtained.

These base paste formulations are then mixed with a catalyst paste formulation comprising siloxane component (A), a suitable catalyst (C) and optionally filler(s), plastiziser(s) and other adjuvants like those described above. By doing this, different curable compositions are obtained having essentially the same consistency but differing from each other by the Shore hardness achieved after hardening.

The term "essentially the same consistency" means that the consistency determined e.g. according to ISO 4823 does not vary by more than 4 mm or by more than 3 mm with respect to each other.

According to a further embodiment, the invention is directed to a process for adjusting the Shore hardness of a composition comprising the steps of a) providing a base formulation (I) and a catalyst formulation (II),
b) mixing the base formulation (I) and the catalyst formulation (II) in a volume ratio from about 1:1 to 30:1,
c) obtaining a cured composition having a Shore A hardness within a range from about 80 to 20 if determined 30 min after mixing,
base formulation (I) comprising
a siloxane component (A) comprising terminal vinyl groups,
a siloxane component (B) comprising Si—H groups, and
a silicone oil (D) having a viscosity at 23[deg.]C. of at least about 600,000 mPa<*>s, catalyst formulation (II) comprising
a siloxane component (A) comprising terminal vinyl groups which might be same or different to the silicone component (A) being present in the base formulation,
a catalyst (C) being able to catalyze a curing reaction between components (A) and (B),
wherein the silicone oil (D) is present in an amount from about 1 to about 20 wt.-% with respect to the weight of the whole composition.

Surprisingly it was found that by varying the amount of the formulations (I) and (II) to be mixed, the Shore hardness can be adjusted over a wide range without negatively affecting properties like elastic recovery or hydrophilicity.

If the amount of base formulation is increased compared to the amount of the catalyst formulation, the Shore hardness can be reduced.

That is, the practitioner can use the same chemical formulation(s) for different purposes. This can simply be done by varying the mixing ratio. This is a big advantage as it can help reducing the variety of dental impression materials needed in the daily practice.

If the practitioner wants to have a comparable soft material (e.g. a material having a Shore hardness A in a range from about 50 to about 67), he can prepare this material simply by increasing the amount of base formulation to be mixed with the catalyst formulation.

On the other hand, if the practitioner wants to have a comparable hard material (e.g. material having a Shore hardness A in a range from about 65 to about 85), he can prepare this material simply by mixing the base formulation with the catalyst formulation in a ratio of 1:1.

In view of the fact that the density of the base formulation is typically nearly identical to the density of the catalyst formulation, it does not really make a difference, if the ratio is based on mass or volume.

Generally, mixing and dosing of the components or pastes can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. Nos. 5,924,600; 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as are described e.g. in U.S. Pat. Nos. 5,249,862; 5,286,105 and 5,332,122. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2.

In practice, the impression material can be syringed through a static or mechanical mixing device into an impression tray or onto the patient's teeth or tissue and placed in the patient's mouth. After the impression material is set, the tray is removed from the patient's mouth and, in instances where the dental practitioner prepares the positive model, it may be preferable to pour the positive model material immediately after removal of the impression from the patient's mouth.

If used in the dental field, the composition can be applied using e.g. the following steps:
providing the composition,
applying the composition to a surface,
letting the composition set.

The surface can be the surface of soft or hard oral tissue, the surface of an impression material, preferably of a cured impression material, the surface of a crown or the surface of a model of a tooth stump.

The composition can be used as dental impression material, or for taking impressions of hard and soft dental tissue or for the production of (temporary or long term) crown and/or bridges.

In the latter case, the composition is used as a mould to be filled with the (temporary or long term) crown and/or bridge material, which is typically based on polymerizable (meth) acrylates.

The composition does typically not contain substances which would be detrimental to the intended purpose, including substances which would be detrimental to the patient's health.

Moreover, with respect to a further embodiment the composition does not contain a silicone elastomer powder, especially an elastomer powder prepared by reacting an organopolysiloxane having at least two olefinic unsaturated groups in a molecule with another organopolysiloxane having at least two silicon-bonded hydrogen atoms in a molecule in the presence of an addition reaction catalyst.

Features and advantages of this invention are further illustrated by the following examples, which are in no way intended to be limiting thereof.

Unless otherwise indicated, all parts and percentages are on a weight basis, all water is deionized water, all molecular weights are weight average molecular weight and all measurements were done at ambient conditions (23° C.).

EXAMPLES

Determination of Setting Time

The Curometer used for measuring the time for onset ($t_A$) of the curing reaction in the examples was a Wallace-Shawburg Curometer (Croydon, GB).

The Curometer measures the cure time of rubber and other cross linking polymers. It can also measure the setting time of resins, cements and dental impression and filling materials. The Curometer can be used for initial research into stock formulation and also for rapid evaluation of cure for quality control.

The terms "cure" or "vulcanisation" usually refers to the change in a network molecular structure. The Curometer measures the times to beginning of cure and end of cure. The shape of the Curometer curve provides a picture of cure characteristic in which the "delay period" and rate of cure can be seen.

For the measurement of the setting behaviour 0.5 g base paste and 0.5 g catalyst paste were mixed and placed within 1 min into the measurement area of the Curometer. The Curometer run time is started with the beginning of the mixing. The measurement was conducted at ambient conditions (23° C.). The accuracy of measurement is about +/−0.2 min.

The end of the setting reaction ($t_e$) was defined as the time after which the curing curve fell below the 10 mm line.

Determination of Consistency

The consistency of the base and the catalyst paste were determined according to ISO 4823 by only using the base or the catalyst paste and are given in mm.

Determination of Shore A Hardness

The Shore A hardness of the compositions was determined according to DIN 53 505 and measured at defined times after mixing of the base and catalyst paste and. The times at which the shore hardness was measured are given in the tables below.

Determination of Stickiness

If desired the stickiness can be determined as follows: haptic (that is, by touching the composition with fingers) or by a rolling ball tack test, e.g. according to ASTM D3121-06 Standard (Test Method for Tack of Pressure-Sensitive Adhesives by Rolling Ball).

A. Preparation of Material—Adjusting Shore Hardness by Adding Silicone Oil:

The base and the catalyst paste used were prepared in a vacuum kneader (<10 mbar) by mixing the raw materials mentioned below to a homogenous paste. The base paste and catalyst paste according to Examples A1-Q1 were filled in a standard polypropylene (PP) jar (Hauschild, 185 ml) and mixed in a mass ratio 1:1 by kneading with the hand.

The base and the catalyst paste used hereafter have been prepared in a vacuum kneader by mixing the respective components to a homogenous paste.

Base Paste Formula A1:

| | |
|---|---|
| Vinyl terminated polydimethylsiloxane (100,000 mPa * s) | 16.7% (weight) |
| Poly(methyl)(hydrogen)siloxane (1.8 mmol/g SiH) | 3.0% (weight) |
| Paraffin oil (110-230 mPa * s) | 7.5% (weight) |
| Hydrophobized crystalline silica filler (<20 μm) | 71.6% (weight) |
| Silicone Surfactant (Silwet L-77) | 0.6% (weight) |
| Flavour | 0.6% (weight) |

To Base Paste A1, polydimethylsiloxane with a viscosity of 10 mPa * s or 2,000,000 mPa * s was added in the amounts given in Table 1 and mixed to a homogenous paste.

TABLE 1

| | Polydimethylsiloxane | |
|---|---|---|
| | 10 mPa * s | 2,000,000 mPa * s |
| Base Paste B1 | — | 2 wt.-% |
| Base Paste C1 | — | 4 wt.-% |
| Base Paste D1 | — | 8 wt.-% |
| Base Paste E1 | — | 15 wt.-% |
| Base Paste F1 | — | 20 wt.-% |
| Base Paste G1 | — | 30 wt.-% |
| Base Paste H1 | 2 wt.-% | — |
| Base Paste I1 | 4 wt.-% | — |
| Base Paste J1 | 8 wt.-% | — |

Catalyst Paste Formula K1:

| | |
|---|---|
| Vinyl terminated polydimethylsiloxane (200 mPa * s) | 4.0% (weight) |
| Vinyl terminated polydimethylsiloxane (100,000 mPa * s) | 16.5% (weight) |
| Paraffin oil (110-230 mPa * s) | 6.9% (weight) |
| Crystalline silica filler (<20 μm) | 71.6% (weight) |
| Platin-Tetramethyldivinyldisiloxane-komplex (1.3 weight-% Pt) in silicone oil | 1.0% (weight) |

To Catalyst Paste K1, polydimethylsiloxane with a 2,000,000 mPa * s was added in the amounts given in Table 2 and mixed to a homogenous paste.

TABLE 2

| | Polydimethylsiloxane 2,000,000 mPa * s |
|---|---|
| Catalyst Paste L1 | 10 wt.-% |

The Shore hardness and consistency of Base Pastes were determined for Base Pastes A1-J1 which were mixed with equal amounts of Catalyst Paste K1.

The results summarized in Table 3 again show that the Shore hardness can be adjusted by addition of a high viscous silicone compound whereas the consistency remains essentially constant and the material remains tack-free.

TABLE 3

| Base Paste | Shore hardness (10'15'/30'/1 d) | Consistency Base Paste [mm] | Stickiness |
|---|---|---|---|
| A1 | 73/73/74/79 | 29 | none |
| B1 | 73/73/73/78 | 30 | none |
| C1 | 69/69/69/74 | 30 | none |
| D1 | 66/66/66/71 | 30 | none |
| E1 | 52/52/52/58 | 31 | none |
| F1 | 48/48/48/53 | 30 | none |
| G1 | 33/39/40/47 | 29 | none |
| H1 | 72/72/72/75 | 33 | slightly |
| I1 | 69/69/70/75 | 35 | sticky |
| J1 | 63/63/64/69 | 38 | very sticky |

"'" means minutes;
"d" means day (24 hours)

The Shore hardness and consistency of Catalyst Paste were determined for Catalyst Pastes K1 and L1 which were mixed with equal amounts of Base Paste F1.

The results summarized in Table 4 again show that the Shore hardness can be adjusted by addition of a high viscous silicone compound whereas the consistency remains essentially constant and the material remains tack-free.

TABLE 4

| Catalyst Paste | Shore hardness (10'15'/30'/1 d) | Consistency catalyst paste [mm] | Stickiness |
|---|---|---|---|
| K1 | 48/48/48/53 | 36 | none |
| L1 | 32/32/32/37 | 35 | none |

"'" means minutes;
"d" means day (24 hours)

The following examples further illustrate the invention.

Base Paste Formula M1:

| | |
|---|---|
| Vinyl terminated polydimethylsiloxane (200 mPa * s) | 2.6% (weight) |
| Vinyl terminated polydimethylsiloxane (100,000 mPa * s) | 14.2% (weight) |
| Poly(methyl)(hydrogen)siloxane (1.8 mmol/g SiH) | 2.4% (weight) |
| Polydimethylsiloxane (2,000,000 mPa * s) | 4.7% (weight) |
| Paraffin oil (110-230 mPas) | 5.9% (weight) |
| Hydrophobized crystalline silica filler (<20 μm) | 67.8% (weight) |
| Pigment | 1.4% (weight) |
| Silicone Surfactant (Silwet L-77) | 0.5% (weight) |
| Flavour | 0.5% (weight) |

Base Paste Formula N1:

| | |
|---|---|
| Vinyl terminated polydimethylsiloxane (100,000 mPa * s) | 15.2% (weight) |
| Poly(methyl)(hydrogen)siloxane (1.8 mmol/g SiH) | 2.7% (weight) |
| Polydimethylsiloxane (2,500,000 mPa * s) | 8.7% (weight) |
| Paraffin oil (110-230 mPas) | 6.8% (weight) |
| Hydrophobized crystalline silica filler (<20 μm) | 65.0% (weight) |
| Pigment | 0.4% (weight) |
| Silicone Surfactant (Silwet L-77) | 0.5% (weight) |
| Flavour | 0.5% (weight) |

Catalyst Paste formula O1:

| | |
|---|---|
| Vinyl terminated polydimethylsiloxane (200 mPa * s) | 3.6% (weight) |
| Vinyl terminated polydimethylsiloxane (100,000 mPa * s) | 15.0% (weight) |
| Paraffin oil (110-230 mPa * s) | 6.3% (weight) |
| Crystalline silica filler (<20 μm) | 74.3% (weight) |
| Platin-Tetramethyldivinyldisiloxane-komplex (1.3 weight-% Pt) in silicone oil | 0.9% (weight) |

Table 5 summarizes setting time and Shore hardness and the consistency of the base pastes.

TABLE 5

| | Base Paste | |
|---|---|---|
| | M1 | N1 |
| Catalyst Paste | O | O |
| Setting time Curometer te (23° C.) [min] | 6.2 | 3.7 |
| Shore hardness (10'/15'/30'/1 d) | 69/70/70/73 | 60/60/60/65 |

"'" means minutes;
"d" means day (24 hours)

Table 6 shows the change of the Curometer setting time to and Shore hardness in dependence on the time for Catalyst Paste O1 and Base Paste M1 which were stored in PP jars at room temperature. These data demonstrate that the formulations are sufficient storage stable.

TABLE 6

| | time [months] | | | |
|---|---|---|---|---|
| | 0 | 0.25 | 1 | 3 |
| Curometer setting time te [min] | 6.2 | 6.0 | 6.3 | 6.3 |
| Shore hardness (10'/15'/30'/1 d) | 69/70/70/73 | 69/69/70/73 | 69/69/69/72 | 67/68/69/72 |

"'" means minutes;
"d" means day (24 hours)

B. Preparation of Material—Adjusting Shore Hardness by Varying Mixing Ratio:

The base and the catalyst paste used hereafter have been prepared in a vacuum kneader (<10 mbar) by mixing the following raw materials to a homogenous paste.

The Base Paste AA1, CC1 and DD1 as well as the Catalyst Paste BB1 according to Table 6 were filled in a standard polypropylene (PP) jars (Hauschild, 185 ml), respectively. Base Paste and Catalyst Paste were mixed in the ratios given in the tables below by hand.

Base Paste Formula AA1:

| | |
|---|---|
| Vinyl terminated polydimethylsiloxane (200 mPa * s) | 2.2% (weight) |
| Vinyl terminated polydimethylsiloxane (100,000 mPa * s) | 12.7% (weight) |

-continued

| | |
|---|---|
| Poly(methyl)(hydrogen)siloxane (SiH content of 1.8 mmol/g) | 2.4% (weight) |
| Polydimethylsiloxane (1,000,000 mPa * s) | 6.0% (weight) |
| Paraffin oil (110-230 mPa * s) | 4.7% (weight) |
| Hydrophobized crystalline silica filler (<20 µm) | 70.3% (weight) |
| Yellow pigment | 0.6% (weight) |
| Silicone surfactant Silwet L-77 | 0.5% (weight) |
| Peppermint flavour | 0.5% (weight) |
| Divinyltetramethyldisiloxane (10% solution in silicone oil) | 0.2% (weight) |

Catalyst Paste Formula BB1:

| | |
|---|---|
| Vinyl terminated polydimethylsiloxane (200 mPa * s) | 4.1% (weight) |
| Vinyl terminated polydimethylsiloxane (100,000 mPa * s) | 13.0% (weight) |
| Paraffin oil (110-230 mPa * s) | 5.7% (weight) |
| Titanium dioxide (<100 µm) | 0.4% (weight) |
| Crystalline silica filler (<20 µm) | 72.1% (weight) |
| Platin-Tetramethyldivinyldisiloxane-komplex (1,3 weight-% Pt) in silicone oil | 4.9% (weight) |

Base Paste Formula CC1:

| | |
|---|---|
| Vinyl terminated polydimethylsiloxane (200 mPa * s) | 2.4% (weight) |
| Vinyl terminated polydimethylsiloxane (100,000 mPa * s) | 13.7% (weight) |
| Mixture of Poly(methyl)(hydrogen)siloxanes (1.8 mmol/g SiH) | 2.4% (weight) |
| Polydimethylsiloxane (1,000,000 mPa * s) | 6.5% (weight) |
| Paraffin oil (110-230 mPas) | 5.0% (weight) |
| Hydrophobized crystalline silica filler (<20 µm) | 68.0% (weight) |
| Yellow pigment | 0.7% (weight) |
| Silicone surfactant Silwet L-77 | 0.5% (weight) |
| Peppermint flavour | 0.5% (weight) |
| Divinyltetramethyldisiloxane (10% solution in silicone oil) | 0.3% (weight) |

Table 7-8 show the Shore hardness after 30 min and 1 day and the curometer setting time to for different mixing ratios of base and catalyst paste. The results shown in the tables below demonstrate that the Shore hardness and the setting time can be adjusted by the mixing ratio of base to catalyst paste for the present examples.

TABLE 7

| | Mixing ratio Base AA1:Catalyst BB1 | | | | |
|---|---|---|---|---|---|
| | 1:1 | 5:1 | 10:1 | 15:1 | 30:1 |
| setting time te Curometer [min] | 2.1 | 5.2 | 10.2 | 16.7 | 43.5 |
| Shore hardness after 30 min/1 d | 73/74 | 61/69 | 57/64 | 55/61 | 27/48 |

TABLE 8

| | Mixing ratio Base CC1:Catalyst BB1 | | | | |
|---|---|---|---|---|---|
| | 1:1 | 5:1 | 10:1 | 15:1 | 30:1 |
| setting time te Curometer [min] | 3.3 | 6.2 | 9.8 | 15.2 | 27.3 |
| Shore hardness after 30 min/1 d | 66/70 | 48/60 | 44/53 | 41/51 | 27/45 |

Table 9 shows the time-depending change of the setting time and Shore hardness of Base Paste AA1 and Catalyst Paste CC1 for a mixing ratio of 5:1 (base:catalyst) at room temperatures. The pastes had been stored in the PP jars mentioned above. The properties did not change significantly, demonstrating the shelf life stability of these formulations.

TABLE 9

| | t [months] | | | | |
|---|---|---|---|---|---|
| | 0 | 0.5 | 1.5 | 3 | 6 |
| Setting time Curometer te [min] | 6.8 | 6.8 | 5.8 | 5.7 | 5.7 |
| Shore hardness after 30 min/1 d | 60/70 | 60/70 | 60/70 | 61/71 | 63/72 |

The following examples further illustrate the invention:

Base Paste A2-C2 as well as Catalyst Paste D2 were filled in a standard PP (poly propylene) jars (Hauschild Comp), respectively. Base Paste and Catalyst Paste were mixed in the weight-ratio 5:1 by hand.

Base Paste Formula A2:

| | |
|---|---|
| Vinyl terminated polydimethylsiloxane (200 mPa * s) | 24.0% (weight) |
| Vinyl terminated polydimethylsiloxane (10,000 mPa * s) | 4.0% (weight) |
| Poly(methyl)(hydrogen)siloxane (SiH content of 1.8 mmol/g) | 10.0% (weight) |
| Hydrophobized fumed silica | 4.0% (weight) |
| Hydrophobized crystalline silica filler (<20 µm) | 57.2% (weight) |
| Silicone surfactant Silwet L-77 | 0.6% (weight) |
| Flavour | 0.2% (weight) |

To Base Paste A2, polydimethylsiloxane with a viscosity of 1,000,000 mPa * s was added in the amounts given in Table 1 and mixed to a homogenous paste.

TABLE 1

| | Polydimethylsiloxane | |
|---|---|---|
| | 10 mPa * s | 1,000,000 mPa * s |
| Base Paste B2 | — | 5 wt.-% |
| Base Paste C2 | — | 10 wt.-% |

Catalyst Paste Formula D2:

| | |
|---|---|
| Vinyl terminated polydimethylsiloxane (2,000 mPa * s) | 35.0% (weight) |
| Hydrophobized fumed silica | 2.0% (weight) |
| Crystalline silica filler (<20 µm) | 60.0% (weight) |
| Platin-Tetramethyldivinyldisiloxane-komplex (1.3 weight-% Pt) in silicone oil | 3.0% (weight) |

The Shore hardness and consistency were determined for Base Pastes A2-C2 which were mixed with Catalyst Paste D2 in a 5:1 weight ratio by hand.

The results summarized in Table 3 again show that the Shore hardness can be adjusted by addition of a high viscous silicone compound whereas the consistency of the mixed pastes remains essentially constant.

TABLE 3

| Base paste | Shore hardness (10'15'/30'/1 d) | Consistency (base + cataylst) paste [mm] |
|---|---|---|
| A2 | 30/30/31/36 | 35 |
| B2 | 25/25/24/30 | 34.5 |
| C2 | 19/19/20/25 | 34 |

"'" means minutes;
"d" means day (24 hours)

The invention claimed is:
1. A composition for taking dental impressions, the composition comprising:
a siloxane component (A) comprising terminal vinyl groups;

a siloxane component (B) comprising Si—H groups;
a catalyst (C) being able to catalyze a curing reaction between components (A) and (B),
a silicone oil (D), and
a surfactant (F),
wherein the silicone oil has a viscosity at 23° C. of at least about 600,000 mPa*s and is present in an amount from about 1 to about 20 wt.-% with respect to the weight of the whole composition.

2. The composition of claim 1, wherein the silicone oil is characterized by at least one of the following features:
viscosity: at least 1,000,000 mPa*s at 23° C.;
molecular weight (Mw): at least about 300,000 g/mol; or
end-capped with trimethylsiloxy-groups.

3. The composition of claim 1, wherein the silicone oil is represented by the following formula:

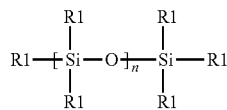

with n being at least about 3500, R1 being independently selected from C1-C6 alkyl or C6-C9 aryl.

4. The composition of claim 1, wherein the weight ratio between the silicone oil (D) and component (B) is from about 1:20 to 20:1.

5. The composition of claim 1, further comprising a filler (E).

6. The composition of claim 1, further comprising adjuvants (G) selected from retarders, rheology modifiers, inhibitors, pigments, plasticisers, dyes, pigments, odorous substances, flavourings, stabilizers, hydrogen scavenger alone or in admixture.

7. The composition of claim 1, further being characterized by at least one of the following features before hardening:
consistency: ≤41 mm or ≤35 mm, measured according to ISO 4823; or
setting time within about 15 min after mixing at temperature in the oral environment (about 36° C.).

8. The composition of claim 1, further characterized by at least one of the following features after hardening:
tensile strength (according to DIN 53504): at least about 0.2 MPa;
elongation at break (according to DIN 53504): at least about 30%;
recovery from deformation (according to DIN 53504): at least about 90%; and
Shore A hardness (according to DIN 53 505; 24h) at least about 20.

9. The composition of claim 1, comprising the components in the following amounts:
siloxane component (A) comprising terminal vinyl groups: from about 10 to about 60 wt.-%;
siloxane component (B) comprising Si—H groups: from about 0.1 to about 20 wt.-%;
catalyst (C): from about 0.0001 to about 0.1 wt.-%;
silicone oil (D): from about 1 to about 20 wt.-%;
filler (E): from about 0 to about 85 wt.-%;
surfactant (F): from about 0 to about 15 wt.-%;
adjuvants (G): from about 0 to about 40 wt.-%; and
F-containing component (H): from about 0 to about 5 wt.-%, wherein wt.-% with respect to the weight of the whole composition.

10. A kit of parts for taking dental impressions, comprising:
a base part having a siloxane component (A) comprising terminal vinyl groups, a siloxane component (B) comprising Si—H groups and a silicone oil (D); and
a catalyst part separate from the base part, the catalyst part having a catalyst (C) being able to catalyze a curing reaction between components (A) and (B), where at least one of the base part or the catalyst part also includes a surfactant (F), and wherein the silicone oil has a viscosity at 23° C. of at least about 600,000 mPa*s and is present in an amount from about 1 to about 20 wt.-% with respect to the weight of the base part and the catalyst part.

11. A method of producing a composition having a consistency of ≤41 mm or ≤35 mm according to ISO 4823, the method comprising:
providing a base paste having:
a siloxane component (A) comprising terminal vinyl groups;
a siloxane component (B) comprising Si—H groups; and
a silicone oil (D), wherein the silicone oil has a viscosity at 23° C. of at least about 600,000 mPa*s and is present in an amount from about 1 to about 20 wt.-% with respect to the weight of the whole composition;
providing a catalyst paste having:
a catalyst (C) and an additional amount of the siloxane component (A) comprising terminal vinyl groups, wherein the siloxane component (A) of the base paste and the siloxane component (A) of the catalyst paste can be chemically the same or different and the catalyst (C) being able to catalyze a curing reaction between components (A) and (B), and
wherein at least one of the base paste or the catalyst paste can further include a filler (E), a surfactant (F), and adjuvants (G); and
mixing the base paste with the catalyst paste to produce the composition having the consistency of ≤41 mm or ≤35 mm according to ISO 4823.

12. The method of claim 11, further including varying the amount of the silicone oil (D) to adjust a Shore hardness A of the composition.

13. The method of claim 12, wherein the Shore hardness A is adjusted in a range from about 85 to about 20.

14. A process for adjusting the Shore hardness A of a composition comprising:
providing a base formulation and a catalyst formulation:
the base formulation (I) having
a siloxane component (A) comprising terminal vinyl groups;
a siloxane component (B) comprising Si—H groups; and
a silicone oil (D) having a viscosity at 23° C. of at least about 600,000 mPa*s and
the catalyst formulation (II) having a siloxane component (A) comprising terminal vinyl groups which might be chemically the same or different than the siloxane component (A) being present in the base formulation and a catalyst (C) being able to catalyze a curing reaction between components (A) and (B);
mixing the base formulation (I) and the catalyst formulation (II) in a volume ratio from about 1:1 to 30:1 to form the composition; and
adjusting the Shore hardness A by varying the amounts of silicone oil (D) in the composition to achieve a cured composition having a Shore A hardness within a range from about 80 to 20 determined 30 min after mixing, and
wherein the silicone oil (D) is present in an amount from about 1 to about 20 wt.-% with respect to the weight of the whole composition.

15. A composition for taking dental impressions, the composition comprising:
a siloxane component (A) comprising terminal vinyl groups;
a siloxane component (B) comprising Si—H groups;
a catalyst (C) being able to catalyze a curing reaction between components (A) and (B),
a silicone oil (D),
wherein the silicone oil has a viscosity at 23° C. of at least about 600,000 mPa*s and is present in an amount from about 1 to about 20 wt. % with respect to the weight of the whole composition, and the composition has at least one of the following features before hardening:
consistency: ≤41 mm or ≤35 mm, measured according to ISO 4823; or
setting time within about 15 min after mixing at temperature in the oral environment (about 36° C.).

16. The composition of claim 15, wherein the silicone oil is characterized by at least one of the following features:
viscosity: at least 1,000,000 mPa*s at 23° C.;
molecular weight (Mw): at least about 300,000 g/mol; or
end-capped with trimethylsiloxy groups.

17. The composition of claim 15, wherein the silicone oil is represented by the following formula:

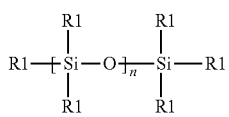

with n being at least about 3500, R1 being independently selected from C1-C6 alkyl or C6-C9 aryl.

18. The composition of claim 15, wherein the weight ratio between the silicone oil (D) and component (B) is from about 1:20 to 20:1.

19. The composition of claim 15, further comprising a filler (E).

20. The composition of claim 15, further comprising a surfactant (F).

21. The composition of claim 15, further comprising adjuvants (G) selected from retarders, rheology modifiers, inhibitors, pigments, plasticisers, dyes, pigments, odorous substances, flavourings, stabilizers, hydrogen scavenger alone or in admixture.

22. The composition of claim 15, further characterized by at least one of the following features after hardening:
tensile strength (according to DIN 53504): at least about 0.2 MPa;
elongation at break (according to DIN 53504): at least about 30%;
recovery from deformation (according to DIN 53504): at least about 90%; and
Shore A hardness (according to DIN 53 505; 24h) at least about 20.

23. The composition of claim 15, comprising the components in the following amounts:
siloxane component (A) comprising terminal vinyl groups: from about 10 to about 60 wt.-%;
siloxane component (B) comprising Si—H groups: from about 0.1 to about 20 wt.-%;
catalyst (C): from about 0.0001 to about 0.1 wt.-%;
silicone oil (D): from about 1 to about 20 wt.-%;
filler (E): from about 0 to about 85 wt.-%;
surfactant (F): from about 0 to about 15 wt.-%;
adjuvants (G): from about 0 to about 40 wt.-%; and
F-containing component (H): from about 0 to about 5 wt.-%, wherein wt.-% with respect to the weight of the whole composition.

24. A composition for taking dental impressions, the composition comprising:
a siloxane component (A) comprising terminal vinyl groups;
a siloxane component (B) comprising Si—H groups;
a catalyst (C) being able to catalyze a curing reaction between components (A) and (B),
a silicone oil (D),
wherein the silicone oil has a viscosity at 23° C. of at least about 600,000 mPa*s and is present in an amount from about 1 to about 20 wt.-% with respect to the weight of the whole composition, where the composition is characterized by at least one of the following features after hardening:
tensile strength (according to DIN 53504): at least about 0.2 MPa;
elongation at break (according to DIN 53504): at least about 30%;
recovery from deformation (according to DIN 53504): at least about 90%; and
Shore A hardness (according to DIN 53 505; 24h) at least about 20.

25. The composition of claim 24, wherein the silicone oil is characterized by at least one of the following features:
viscosity: at least 1,000,000 mPa*s at 23° C.;
molecular weight (Mw): at least about 300,000 g/mol; or
end-capped with trimethylsiloxy groups.

26. The composition of claim 24, wherein the silicone oil is represented by the following formula:

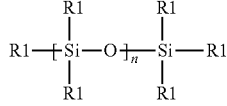

with n being at least about 3500, R1 being independently selected from C1-C6 alkyl or C6-C9 aryl.

27. The composition of claim 24, wherein the weight ratio between the silicone oil (D) and component (B) is from about 1:20 to 20:1.

28. The composition of claim 24, further comprising a filler (E).

29. The composition of claim 24, further comprising a surfactant (F).

30. The composition of claim 24, further comprising adjuvants (G) selected from retarders, rheology modifiers, inhibitors, pigments, plasticisers, dyes, pigments, odorous substances, flavourings, stabilizers, hydrogen scavenger alone or in admixture.

31. The composition of claim 24, further being characterized by at least one of the following features before hardening:

consistency: ≤41 mm or ≤35 mm, measured according to ISO 4823; or setting time within about 15 min after mixing at temperature in the oral environment (about 36° C.).

32. The composition of claim 24, comprising the components in the following amounts:

siloxane component (A) comprising terminal vinyl groups: from about 10 to about 60 wt.-%;

siloxane component (B) comprising Si—H groups: from about 0.1 to about 20 wt.-%;

catalyst (C): from about 0.0001 to about 0.1 wt.-%;

silicone oil (D): from about 1 to about 20 wt.-%;

filler (E): from about 0 to about 85 wt.-%;

surfactant (F): from about 0 to about 15 wt.-%;

adjuvants (G): from about 0 to about 40 wt.-%; and

F-containing component (H): from about 0 to about 5 wt.-%, wherein wt-% with respect to the weight of the whole composition.

33. A composition for taking dental impressions, the composition comprising:

about 10 to about 60 wt.-% of a siloxane component (A) comprising terminal vinyl groups;

about 0.1 to about 20 wt.-% of a siloxane component (B) comprising Si—H groups;

about 0.0001 to about 0.1 wt.-% of a catalyst (C) being able to catalyze a curing reaction between components (A) and (B), about 1 to about 20 wt.-% of a silicone oil (D), about 0 to about 15 wt.-% of a surfactant (F), wherein the silicone oil has a viscosity at 23° C. of at least about 600,000 mPa*s and is present in an amount from about 1 to about 20 wt.-% with respect to the weight of the whole composition, and the wt % is with respect to the weight of the whole composition.

34. The composition of claim 33, wherein the silicone oil is characterized by at least one of the following features:

viscosity: at least 1,000,000 mPa*s at 23° C.;

molecular weight (Mw): at least about 300,000 g/mol; or end-capped with trimethylsiloxy-groups.

35. The composition of claim 33, wherein the silicone oil is represented by the following formula:

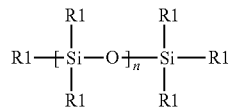

with n being at least about 3500, R1 being independently selected from C1-C6 alkyl or C6-C9 aryl.

36. The composition of claim 33, wherein the weight ratio between the silicone oil (D) and component (B) is from about 1:20 to 20:1.

37. The composition of claim 33, further comprising a filler (E).

38. The composition of claim 33, further comprising a surfactant (F).

39. The composition of claim 33, further comprising adjuvants (G) selected from retarders, rheology modifiers, inhibitors, pigments, plasticisers, dyes, pigments, odorous substances, flavourings, stabilizers, hydrogen scavenger alone or in admixture.

40. The composition of claim 33, further being characterized by at least one of the following features before hardening:

consistency: ≤41 mm or ≤35 mm, measured according to ISO 4823; or setting time within about 15 min after mixing at temperature in the oral environment (about 36° C.).

41. The composition of claim 33, further characterized by at least one of the following features after hardening:

tensile strength (according to DIN 53504): at least about 0.2 MPa;

elongation at break (according to DIN 53504): at least about 30%;

recovery from deformation (according to DIN 53504): at least about 90%; and

Shore A hardness (according to DIN 53 505; 24h) at least about 20.

42. The composition of claim 33, further including:

about 0 to about 85 wt.-% of a filler (E), about 0 to about 40 wt.-% of a adjuvants (G), about 0 to about 5 wt.-% of an F-containing component (H), the wt % with respect to the weight of the whole composition, where the wt-% is with respect to the weight of the whole composition.

* * * * *

UNITED STATES PATENT AND TRADEMARK OFFICE
CERTIFICATE OF CORRECTION

| | | |
|---|---|---|
| PATENT NO. | : 8,980,973 B2 | |
| APPLICATION NO. | : 14/124456 | |
| DATED | : March 17, 2015 | |
| INVENTOR(S) | : Peter Osswald et al. | |

It is certified that error appears in the above-identified patent and that said Letters Patent is hereby corrected as shown below:

On the title page item (57)

Line 7, delete "DEG" and insert -- deg. --, therefor.

Line 8, delete "wt. %" and insert -- wt.-% --, therefor.

In the specification

<u>Column 1</u>

Lines 21-22, delete "azridino-" and insert -- aziridino- --, therefor.

<u>Column 1</u>

Line 23, delete "hybride" and insert -- hybrid --, therefor.

<u>Column 1</u>

Line 60, delete "divinylterminated" and insert -- divinyl terminated --, therefor.

<u>Column 2</u>

Line 2, delete "hydrophlized" and insert -- hydrophilized --, therefor.

<u>Column 2</u>

Line 33, delete "mPa<*>s" and insert -- mPa*s --, therefor.

Signed and Sealed this
Twenty-fourth Day of May, 2016

Michelle K. Lee
*Director of the United States Patent and Trademark Office*

Column 2

Line 34, delete "mPa<*>s" and insert -- mPa*s --, therefor.

Column 2

Line 53, delete "mPa<*>s" and insert -- mPa*s --, therefor.

Column 4

Lines 50-51, delete "Silwett L-77" and insert -- Silwet L-77 --, therefor.

Column 10

Line 6, delete "3,715,334;" and insert -- 3,715,334, --, therefor.

Column 10

Line 15, delete "the the" and insert -- the --, therefor.

Column 12

Line 49, delete "acyll" and insert -- acyl --, therefor.

Column 12

Line 65, delete "methyl-I-butyne" and insert -- methyl-1-butyne --, therefor.

Column 13

Line 1, delete "diacetats" and insert -- diacetates --, therefor.

Column 13

Line 2, delete "plastizers" and insert -- plasticizers --, therefor.

Column 13

Line 14, delete "methyl-I-" and insert -- methyl-1- --, therefor.

Column 13

Line 15, delete "cyclohexane-I-ol," and insert -- cyclohexane-1-ol, --, therefor.

Column 13

Line 15, Delete "dimethyl-I-hex-" and insert -- dimethyl-1-hex- --, therefor.

Column 13

Line 16, delete "methyl-I-pentyne" and insert -- methyl-1-pentyne --, therefor.

Column 13

Line 17, delete "based an" and insert -- based on --, therefor.

Column 13

Line 52, delete "CF$_2$)—" and insert -- CF$_2$)$_u$— --, therefor.

Column 13

Line 65, delete "CF$_2$)—" and insert -- CF2)$_u$— --, therefor.

Column 15

Line 10, delete "<41" and insert -- ≤41 --, therefor.

Column 15

Line 10, delete "<35" and insert -- ≤35 --, therefor.

Column 15

Line 20, delete "mPa<*>s," and insert -- mPa*s, --, therefor.

Column 15

Line 45, delete "plastiziser(s)" and insert -- plasticizer(s) --, therefor.

Column 15

Line 52, delete "plastiziser(s)" and insert -- plasticizer(s) --, therefor.

Column 16

Line 7, delete "silioxane" and insert -- siloxane --, therefor.

Column 16

Line 10, delete "mPa<*>s," and insert -- mPa*s, --, therefor.

Column 16

Line 53, delete "5,924,600;" and insert -- 5,924,600, --, therefor.

Column 16

Line 60, delete "5,249,862;" and insert -- 5,249,862, --, therefor.

Column 17

Lines 23-26, delete "In the latter case, the composition...based on polymerizable (meth)acrylates." and insert the same on Col. 17, Line 22, after "bridges." as the continuation of same Paragraph.

Column 17

Lines 31-37, delete "Moreover, with respect to a further embodiment...the presence of an addition reaction catalyst." and insert the same on Col. 17, Line 30, after "health." as the continuation of same Paragraph.

Column 20

Line 34, delete "to" and insert -- te --, therefor.

Column 21

Line 39, delete "to" and insert -- te --, therefor.

Column 22

Line 55 (Approx.), delete "cataylst)" and insert -- catalyst) --, therefor.

In the claims

Column 23

Line 15, In Claim 2, delete "trimethylsiloxy-groups." and insert -- trimethylsiloxy groups. --, therefor.

Column 23

Line 52, In Claim 8, delete "DIN 53 505;" and insert -- DIN 53505; --, therefor.

Column 24

Line 28, In Claim 11, before "providing" insert -- and --.

Column 25

Line 2, In Claim 14, delete "20determined" and insert -- 20 determined --, therefor.

Column 25

Line 60, In Claim 22, delete "DIN 53 505;" and insert -- DIN 53505; --, therefor.

Column 26

Line 32, In Claim 24, delete "DIN 53 505;" and insert -- DIN 53505; --, therefor.

Column 27

Line 40, In Claim 33, delete "wt. %" and insert -- wt.-% --, therefor.

Column 27

Line 46, In Claim 34, delete "trimethylsiloxy-groups." and insert -- trimethylsiloxy groups. --, therefor.

Column 28

Line 38, In Claim 41, delete "DIN 53 505;" and insert -- DIN 53505; --, therefor.

Column 28

Line 44, In Claim 42, delete "wt. %" and insert -- wt.-% --, therefor.